United States Patent [19]
Drucker

[11] Patent Number: 5,846,937
[45] Date of Patent: Dec. 8, 1998

[54] METHOD OF USING EXENDIN AND GLP-1 TO AFFECT THE CENTRAL NERVOUS SYSTEM

[75] Inventor: Daniel J. Drucker, Toronto, Canada

[73] Assignee: 1149336 Ontario Inc., Toronto, Canada

[21] Appl. No.: 811,066

[22] Filed: Mar. 3, 1997

[51] Int. Cl.$^6$ .......................... A61K 38/26; C07K 14/605
[52] U.S. Cl. .............................. 514/12; 514/2; 530/350; 530/399
[58] Field of Search .......................... 514/2, 12; 530/350, 530/324

[56] References Cited

U.S. PATENT DOCUMENTS

| | | |
|---|---|---|
| 5,118,666 | 6/1992 | Habener . |
| 5,120,712 | 6/1992 | Habener . |
| 5,424,286 | 6/1995 | Eng . |
| 5,512,549 | 4/1996 | Chen et al. . |
| 5,545,618 | 8/1996 | Buckley et al. . |
| 5,574,008 | 11/1996 | Johnson et al. . |
| 5,614,492 | 3/1997 | Habener . |

OTHER PUBLICATIONS

Calvo et al., "Structural Characterization by Affinity Cross–Linking of Glucagon–Like Peptide–1(7–36) Amide Receptor in Rat Brain," *Journal of Neurochemistry* 64(1):299–306.

Komatsu et al., 1989, "Glucagonostatic and Insulinotropic Action of Glucagonlike Peptide I–(7–36)–Amide," *Diabetes* 38:902–905.

Larsen et al., 1997, "Distribution of Glucagon–Like Peptide–1 and Other Preproglucagon–Derived Peptides in the Rat Hypothalamus and Brainstem," *Neuroscience* 77(1):257–270.

Oben et al., 1991, "Effect of the entero–pancreatic hormones, gastric inhibitory polypeptide and glucagon–like polypeptide–1(7–36) amide, on fatty acid synthesis in explants of rat adipose tissue," *Journal of Endocrinology* 130:267–272.

Schmidtler et al., 1994, "Rat parietal cell receptors of GLP–1–(7–36) amide: Northern blot, cross–linking, and radioligand binding," American Physiological Society pp. G423–G432.

Weir et al., 1988, "Glucagonlike Peptide I (7–37) Actions on Endocrine Pancreas," pp. 338–341.

*Primary Examiner*—Marianne P. Allen
*Attorney, Agent, or Firm*—Pennie & Edmonds LLP

[57] ABSTRACT

Agonists of the incretin GLP-1 have been found to have a sedative or anxiolytic effect on the mammalian central nervous system. Additionally, exendin has been found to have an independent sedative effect on the mammalian central nervous system. Conversely, antagonists of GLP-1 increase nervous system activity. The invention relates, in one aspect, to the use of GLP-1 agonists and antagonists to affect the arousal state of the mammalian central nervous system. The invention also relates to novel transgenic mammals in which the GLP-1 receptor gene has been disrupted.

10 Claims, 1 Drawing Sheet

METHOD OF USING EXENDIN AND GLP-1 TO AFFECT THE CENTRAL NERVOUS SYSTEM

FIELD OF THE INVENTION

The present invention relates to methods of altering the activity of the mammalian central nervous system. Specifically, the invention relates to the use of exendin or GLP-1, and agonists and antagonists thereof, as either anxiolytic or stimulatory effectors of the central nervous system. The invention also relates to novel transgenic mammals in which the GLP-1 receptor gene has been disrupted.

BACKGROUND TO THE INVENTION

Regulation of nutrient-induced insulin secretion is dependent upon the secretion of incretins, gut-derived peptides that potentiate insulin secretion from the pancreatic islets. Creutzfeldt et al., 1985, Diabetologia 28:565–573. The incretins gastric inhibitory polypeptide (GIP) and GLP-1 are released from enteroendocrine cells and stimulate insulin release following oral but not intravenous glucose administration in both humans and rodents. See for review Fehmann et al., 1995, Endocrine Rev. 16:390–410. GLP-1 also inhibits eating in rodents and lowers blood glucose in patients with both non-insulin-dependent diabetes mellitus and insulin-dependent diabetes mellitus. Thus, GLP-1 has been proposed for use in the treatment of diabetes. GLP-1 is also produced by neurons in the central nervous system. Jin et al., 1988, J. Comp. Neurol. 271:519–532; Kreymann et al., 1989, Brain Res. 502:325–331.

GLP-1 may also have other important extrapancreatic effects such as inhibition of gastric emptying and stimulation of insulin-dependent glucose uptake. Willms et al., 1996, J. Clin. Endocrinol. Metab. 81:327–332; D'Allesio et al., 1995, Diabetes 44:1433–37. However, the mechanisms responsible for GLP-1 mediated effects on glucose uptake have not been clearly elucidated.

Signalling by GLP-1 is transduced through a single G-protein-linked receptor predominantly expressed in pancreatic islets, lung, stomach and brain. Thorens et al., 1992, PNAS:USA 89:8641–8645. In dispersed mammalian parietal cells, binding of GLP-1 to the GLP-1 receptor (GLP-1R) causes cAMP-dependent $H^+$ production. Schmidtler et al., 1991, Am. J. Physiol. 260:G940. GLP-1 is not the only naturally occurring ligand which binds the GLP-1R. Exendin 3 and exendin 4, biologically active peptides first isolated from Helodermatidae lizard venoms, have also been shown to bind GLP-1R and stimulate cAMP-dependent $H^+$ production in dispersed mammalian parietal cells.

Exendins 3 and 4 are both 39 amino acid peptides (differing at residues 2 and 3) which are approximately 53% homologous to GLP-1. They act as potent agonists of GLP-1 activity. See for review Raufman, 1996, Regulatory Peptides 61:1–18. Notably, an N terminally truncated derivative of exendin, known as exendin(9–39 amino acids), is an inhibitor of both exendins and GLP-1. Although the amino-terminally truncated lizard peptide exendin(9–39 amino acids) binds to the GLP-1R, functions as a GLP-1R antagonist, and inhibits GLP-1-stimulated cAMP formation, experiments with the cloned human islet GIP receptor demonstrate that exendin(9–39) also functions as a GIP receptor antagonist.

The presence of both GLP-1 and GLP-1R in the brain led some researchers to speculate that GLP-1 may have a more central role in the control of satiety. Indeed, intracerebroventricular (ICV) injections of GLP-1 elicited increases in neural activity, as assessed by c-Fos immunohistochemistry. Van Dijk et al., 1996, Am. J. Physiol. 271:R1096-R1100. Recent experiments demonstrate that ICV administration of GLP-1 inhibits feeding in rats. Turton et al., 1996, Nature 379:69–72. Additionally, ICV administration of GLP-1 to rats caused a reduction in locomotor activity indistinguishable to that seen in rats after ingestion of a palatable meal. Moreover, the GLP-1R antagonist exendin(9–39) doubled food intake following ICV injection in fasted rats and potentiated the neuropeptide Y (NPY)-mediated stimulation of food intake. Id. Therefore, these investigators speculated that activation of the GLP-1/GLP-1R pathway caused a satiety effect in the brain, whereas blocking the GLP-1R with a GLP-1 antagonist prevented the satiety effect.

However, since exendin(9–39) is also a GIP receptor antagonist, studies with exendin(9–39) do not permit definitive conclusions about the action of GLP-1 in vivo. Further, it is unclear whether these effects of GLP-1, exendin 4, and exendin(9–39) are actually due to direct regulation of satiety. Instead, GLP-1 and exendin may cause a more generalized effect such as development of a conditioned taste aversion, similar to that of the known emetic agent $LiCl_3$. See "Scientific Correspondence," 1997, Nature 385:214. Moreover, the disruption of GLP-1/GLP-1R signalling in the central nervous system is not associated with perturbation of feeding behavior or obesity in vivo. Schrocchi et al., 1996, Nature Medicine 2:1254–1258. Therefore, the biological importance of GLP-1 as neuropeptide that specifically inhibits food intake remains controversial.

The present invention is directed towards achieving a more definitive resolution of the effects of GLP-1, exendins, and related agonists and antagonists, on the brain and central nervous system. Knowledge of these effects will not only provide opportunities for new therapies, but will also inform about the potential side effects of proposed uses of incretins.

SUMMARY OF THE INVENTION

Accordingly, the invention is based in part upon the discovery and characterization of a novel effect of incretins, and agonists and antagonists thereof, in the mammalian central nervous system. Surprisingly, administration of GLP-1 and exendin agonists and antagonists has been found to affect not only the in vivo satiety response, but also to have profound effects on the state of activation of the central nervous system. Although this effect is mediated in part by the GLP-1R, changes in the activation of the central nervous system may also be achieved independently of the GLP-1R. These discoveries have far-reaching implications for the interaction between the gastric and central nervous systems.

In one aspect of the invention, there is provided a method of sedating a mammalian subject with an abnormality resulting in increased activation of the central or peripheral nervous system. The method comprises administering an exendin or GLP-1, or an agonist of exendin or GLP-1, to the subject in an amount sufficient to produce a sedative or anxiolytic effect on the subject. The exendin or GLP-1, or the agonist of exendin or GLP-1, may be administered intracerebroventriculary, orally, subcutaneously, intramuscularly, or intravenously. Such methods are useful to treat or ameliorate nervous system conditions such as anxiety, movement disorder, aggression, psychosis, seizures, panic attacks, hysteria and sleep disorders.

In a related aspect, the invention encompasses a method of increasing the activity of a mammalian subject, comprising administering an antagonist of exendin or GLP-1 to the subject in an amount sufficient to produce an activating effect on the subject. Preferably, the subject has a condition resulting in decreased activation of the central or peripheral nervous system. A particularly preferred antagonist is exendin(9–39). This aspect of the invention finds particular use in the treatment or amelioration of depression, schizoaffective disorders, sleep apnea, attention deficit syndromes with poor concentration, memory loss, forgetfulness, and narcolepsy, to name just a few conditions in which arousal of the central nervous system may be advantageous.

In yet another aspect, the invention encompasses transgenic non-human mammals containing a genetically engineered GLP-1R gene allele in which normal function of the GLP-1R gene product is destroyed. Even more preferred are transgenic non-human mammals which contain a homozygous "knock-out" of the GLP-1R. Such transgenic animals have a number of uses, including as a vehicle from which to identify the mammalian exendin receptor, or to elucidate the activity of exendin in the mammal apart from its interactions with the GLP-1/GLP-1R signalling pathway.

DETAILED DESCRIPTION OF THE INVENTION

Figure 1:
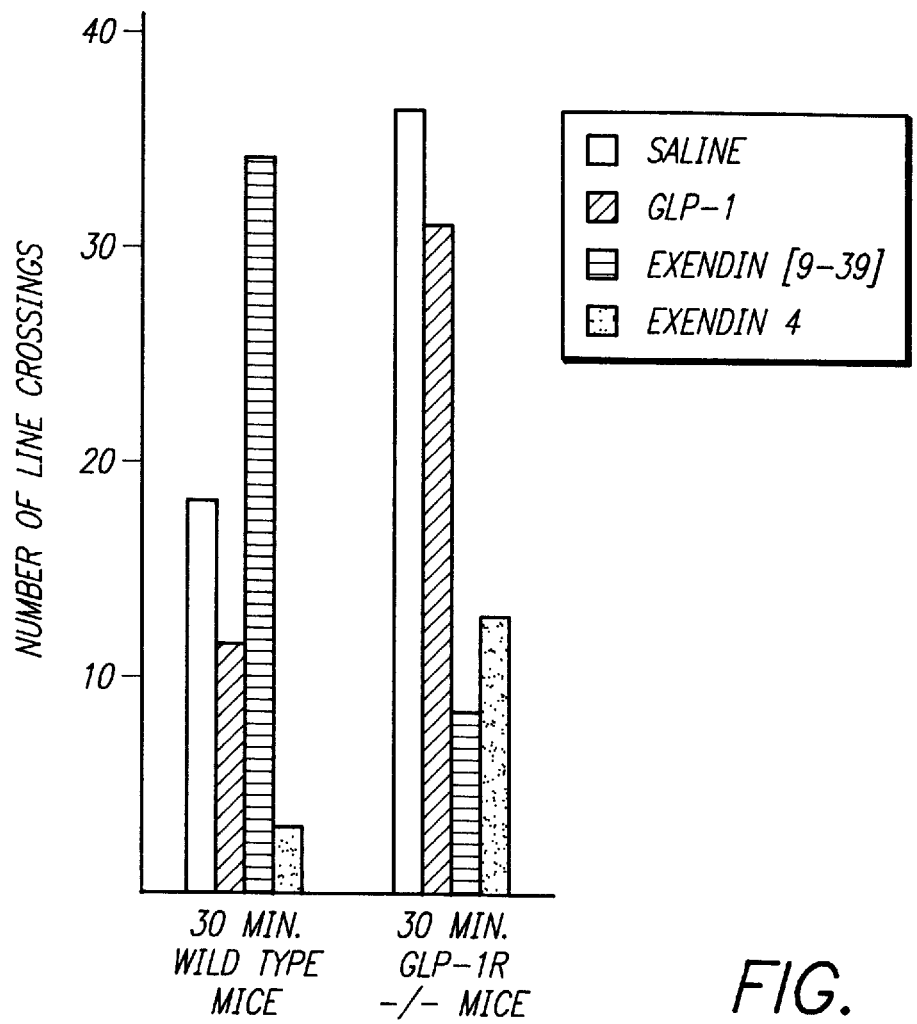
FIG. 1 is an assessment of the activity of both wild-type mice, and GLP-1R$^{-/-}$ knockout mice, determined by number of line crossing events, 30 minutes after ICV injection of saline, human GLP-1 [5 µg/5 µl; Glucagon-like Peptide 1 (7–36) amide], Exendin(9–39) amide [10 µg/5 µl], or Exendin-4 amide [15 µg/5 µl], as indicated.

The invention is based, in part, on the novel observation that both exendin and GLP-1, and agonists of the same, have sedative-like effects on the mammalian nervous system. In a related aspect, the invention concerns the discovery that GLP-1 antagonists and exendin antagonists, for example exendin(9–39), arouse or activate the mammalian nervous system.

These observations derive from studies administering either the GLP-1R agonist exendin 4, the GLP-1R agonist GLP-1 (7–36 amino acid amide), and the GLP-1R antagonist exendin(9–39) directly into the mammalian brain. ICV injection of either the agonist exendin or the agonist GLP-1 (7–36) amide produced a calming effect in mice associated with visibly decreased activity and movement. Conversely, administration of the antagonist exendin(9–39) increased activity.

These unexpected results are reinforced by the observation that mice which are homozygous null for the GLP-1R protein exhibit increased activity compared to wild-type mice. Furthermore, contrary to what would have been predicted if activation of GLP-1R was responsible for the satiety response, transgenic mice disrupted in the GLP-1R/GLP-1 signalling pathway exhibit normal feeding behaviours and are not obese, indicating that GLP-1 does not play a central role in the control of satiety. Instead, such transgenic mice are visibly more nervous and anxious than wild-type mice. For example, when wild-type mice are injected daily with saline over a two week period, they gain weight. However, GLP-1R knockout mice subject to the same saline injection regime actually lose weight. Thus, the GLP-1R appears to play a normal role in regulating activity in the central nervous system.

Surprisingly, administration of exendin agonist (exendin 4) to mice mutant for the GLP-1R protein still resulted in a sedative effect, indicating that exendin can also independently induce sedative effects through a different receptor and/or mechanism than the GLP-1R. Therefore, yet another aspect of the invention based on this discovery is the use of exendins, including both exendin 3 and exendin 4, to exert a sedative effect on the mammalian brain.

Another aspect of the invention is the generation of novel transgenic non-human mammals engineered to have a mutant GLP-1R. In a preferred embodiment of the invention, as exemplified by way of a specific example below, transgenic mice containing a null mutation in the GLP-1R gene are provided. Such transgenic mammals are particularly useful in elucidating the action of GLP-1 and exendin on the mammalian brain, and are also useful as a cloning vehicle for identifying the mammalian exendin receptor protein and gene.

Various aspects of the invention are described in greater detail in the subsections below.

Generation of Transgenic Non-Human Animals

A particularly useful aspect of the present invention is transgenic animals which carry a mutated allele of the GLP-1R gene. Such animals are valuable for a variety of uses described below in the following section. Animals of any species, including, but not limited to, mice, rats, rabbits, guinea pigs, pigs, micro-pigs, goats, and non-human primates, e.g., baboons, monkeys, and chimpanzees, may be used to generate transgenic animals modified or mutated for their GLP-1R gene. Mutations are introduced to destroy a normal function of the GLP-1R gene. Such functions include insertion of the GLP-1R gene product into the cell membrane, expression of GLP-1R on the cell surface, the ability of the GLP-1R to bind an extracellular agonist or antagonist, and the ability of the GLP-1R to transduce an intracellular signal.

Any technique known in the art may be used to introduce a mutant or null GLP-1R transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry a mutant GLP-1R transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art.

Preferably, the mutant GLP-1R gene transgene is integrated into the chromosomal site of the endogenous GLP-1R gene through gene targeting. Briefly, when such a technique is to be utilized, vectors containing some nucleotide sequences homologous to the endogenous GLP-1R gene are designed for the purpose of integrating, via homologous recombination with chromosomal sequences, into and disrupting the function of the nucleotide sequence of the endogenous GLP-1R gene. This preferred embodiment is illustrated below by way of a working example. The transgene may also be selectively introduced into a particular cell type, thus inactivating the endogenous GLP-1R gene in only that cell type, by following, for example, the teaching of Gu et al. (Gu, et al., 1994, Science 265: 103–106). The regulatory sequences required for such a cell-type specific inactivation will depend upon the particular cell type of interest, and will be apparent to those of skill in the art.

Once transgenic animals have been generated, the expression of the recombinant GLP-1R gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of normally GLP-1R gene-expressing tissue, may also be evaluated immunocytochemically using antibodies specific for the GLP-1R.

Uses of Transgenic Animals

The transgenic animals are useful for a number of purposes. For example, the transgenic animals of the invention may be used not only for studying the GLP-1/GLP-1R pathway, but also to elucidate the effects of exendin on the mammalian nervous system independent of exendin's effects on the GLP-1/GLP-1R axis. Since exendins 3 and 4 are approximately 52% homologous to GLP-1, and both exendins have been shown to bind to the GLP-1R, it has been extremely difficult to elucidate the full role of exendins in mammals.

The transgenic mammals of the invention eliminate the background activity from the GLP-1R. One particular advantageous use of the transgenic animals of the invention is that they may be used as a vehicle to clone the mammalian exendin receptor(s). As shown by the present invention, the mammalian exendin receptor also is involved in altering CNS activity. Thus, the exendin receptor is an additional target for effecting changes in the nervous system and the gut/brain axis.

For example, brain tissue from the GLP-1R$^{(-/-)}$ knockout mice may be used to identify exendin receptors, initially by demonstrating the presence of exendin binding sites using in situ autoradiography with a labeled exendin polypeptide probe. cDNA libraries prepared from brain regions that contained the exendin binding sites (in the absence of the GLP-1R protein) could then be screened under low stringency hybridization conditions with a polynucleotide encoding the GLP-1R as a probe. Since GLP-1 and exendins share approximately 52% amino acid homology, and exendin peptide binds to the GLP-1R, one would predict that the exendin receptor will also show homology to the known GLP-1R. Alternatively, PCR could be performed using primers complementary to transmembrane domains 2 or 3 and 6 or 7 of the GLP-1R which are likely be homologous to the putative exendin receptor.

Such transgenic non-human mammals are also useful to determine whether exendin or GLP-1 exert their effects through other non-obvious mechanisms or novel receptors. For example, as described below, both the testis and ovaries in the GLP-1R$^{-/-}$ mice are smaller, implying that they have a defective gonadal maturation or sexual maturation. This effect of GLP-1 was not known prior to detailed analysis of the GLP-1R phenotype. The transgenic animals can thus be used to delineate novel, previously unappreciated, actions of GLP-1 and/or exendin.

Treatment of Nervous System Disorders

The invention encompasses methods and compositions for altering the activity of the mammalian central nervous system. For example, by activating either the GLP-1R or the exendin receptor with receptor agonist, or stimulating activity of the GLP-1R or exendin receptor pathways (e.g., by binding a ligand to the receptor which transduces a signal or by targeting downstream signaling events) in neuronal cells, a sedative or anxiolytic effect on the central and/or peripheral nervous systems may be achieved. Alternatively, the state of arousal of the central nervous system in a subject may be increased by administering an antagonist to GLP-1 or exendin. Different approaches are discussed below.

Inducing a Sedative or Anxiolytic Effect on the CNS.

Any method which activates the GLP-1R and/or mammalian exendin receptor can be used to induce a sedative effect on the central and/or peripheral nervous system of a subject. Such approaches may be used to ameliorate nervous conditions requiring sedation or the alleviation of anxiety. These conditions include, but are not limited to, anxiety, movement disorder, aggression, psychosis, seizures, panic attacks, hysteria, and sleep disorders.

As shown below by way of a working example, both GLP-1 (7–36) amide and exendin 4 induce a sedative effect in vivo. A number of other GLP-1R agonists are also known. Biologically active forms and derivatives of GLP-1 hormone which are useful in the methods of the invention are described Habener, U.S. Pat. Nos. 5,120,712 and 5,118,666, Chen et al., U.S. Pat. No. 5,512,549, Buckley et al., U.S. Pat. No. 5,545,618, and Johnson et al. U.S. Pat. No. 5,574,008. Exendin 4(2–39) is also an agonist of the GLP-1R, as well as chimeras of GLP-1 and exendin 4, such as GLP-1(3–36)/extendin(31–39). See for example abstracts by Montrose-Rafizadeh et al. and Eng, J. in Diabetes, 45 (supplement 2):

152A. Similarly, exendin 3, also isolated from lizard venom, is yet another GLP-1R agonist which may be used to induce a sedative effect on the central and/or peripheral nervous system in vivo.

In fact, any compound or peptide capable of binding to and activating either the GLP-1R or the exendin receptor is useful in the methods of the invention. For example, many transmembrane receptors are activated upon binding of an antibody fragment to the extracellular domain of the receptor. The methods of the invention encompass such antibodies to the exendin or GLP-1R extracellular domain, including humanized antibodies, antibody fragments such as Fab fragments, and single-chain antibodies. However, any antibodies to the extracellular domain should be characterized as either agonists or antagonists of the receptor using a cellular assay, e.g., the rat acinar cell assay of cAMP-dependent H$^+$ production.

Therapeutic treatment with GLP-1 and/or exendin agonists is administered so as to reduce or eliminate the symptoms in these patients associated with their nervous conditions. For example, GLP-1 or exendin is administered to a patient with a movement disorder such as dystonia in an amount sufficient to reduce the occurrence of aberrant and involuntary movements associated with the condition. Additionally, GLP-1 or exendin may be administered to patients with a sleep disorder so as to induce sleep and thereby improve the mental status of such patients. Guidance for formulations, routes of administration, and dosages is provided below.

Activating The CNS.

Since mammals carrying a homozygous mutation which inactivates the GLP-1R exhibit increased arousal levels as demonstrated by increased activity, this property can be exploited to treat diseases associated with a depression of central nervous system activity. Additionally, antagonists of the GLP-1R and/or the exendin receptor also will activate the central nervous system in vivo. Methods of reducing, blocking or antagonizing GLP-1R or exendin receptor activity may be used to induce arousal for the treatment or amelioration of depression, schizoaffective disorders, sleep apnea, attention deficit syndromes with poor concentration, memory loss, forgetfulness, and narcolepsy, to name just a few. The therapeutic efficacy of the antagonist treatment may be monitored by patient interview to assess their condition, by psychological/neurological testing, or by amelioration of the symptoms associated with these conditions. For example, treatment of narcolepsy may be assessed by monitoring the occurrence of narcoleptic attacks. As another example, effects of antagonists of GLP-1 or exendin on the ability of a subject to concentrate, or on memory capacity, may be tested using any of a number of diagnostic tests well known to those of skill in art.

A particularly potent antagonist of the GLP-1R and exendin receptor for use in the method of the invention is exendin(9–39). Other modifications and/or peptide fragments of GLP-1 and/or exendin may be useful as antagonists, and may be identified by assays well known to those of skill in the art. For example, GLP-1(9–36) amide or GLP-1(9–37) are known antagonists of the GLP-1R. Exendin 4(3–39) is yet another known antagonist of the GLP-1 receptor, as are exendin(4–39) through exendin(8–39). See for example Montrose-Rafizadeh et al., supra. Additionally, as noted above, certain antibodies to the extracellular domains of the GLP-1R and exendin receptor may, instead of activating signal transduction through these receptors, antagonize signal transduction.

Pharmaceutical Preparations and Methods of Administration

Exendin and GLP-1 agonists, including polypeptides, peptides, and fusion proteins, or compounds that are determined to antagonize exendin or GLP-1 activity such as exendin(9–39) or antibodies, can be administered to a patient at therapeutically effective doses to treat or ameliorate nervous system disorders. A therapeutically effective dose refers to that amount of the compound sufficient to result in amelioration of symptoms of nervous system disorders.

Effective Dose.

Numerous factors may be taken into consideration by a clinician when determining an optimal dosage for a given subject. Primary among these is the amount of peptide hormone normally produced by the body. Circulating levels of GLP-1 in the body are normally in the range of 2 to 50 picoMoles per liter, depending upon the assay methodology used. Additional factors include the size of the patient, the age of the patient, the general condition of the patient, the particular disease being treated, the severity of the disease, the presence of other drugs in the patient, the in vivo activity of the peptide or peptide analog and the like. The trial dosages would be chosen after consideration of the results of animal studies and the clinical literature with respect to administration of peptide hormones and peptide hormone secretagogues. It will be appreciated by the person of ordinary skill in the art that information such as binding constants and Ki derived from in vitro binding competition assays may also be used in calculating dosages.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of action, the nervous system, in order to minimize potential damage to other cells and tissues and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from animal studies. A dose may be formulated in animal models to achieve a circulating plasma concentration range that includes the $IC_{50}$ (i.e., the concentration of the test compound which achieves a half-maximal inhibition of symptoms). Such information can be used to more accurately determine useful doses in humans. Levels in plasma may be measured, for example, by high performance liquid chromatography.

Guidance for determining dosages of GLP-1(7–36) amide appropriate for subcutaneous and intravenous administration in humans may be found in the following references: Ritzel et al., 1995, Diabetologia 38:720–725; Nauk et al., 1993, Diabetologia 36: 741–744; Willms et al., 1996, 81:327; Dupre et al., 1995, Diabetes 44:626; and Nauck et al., 1996, Diabetologia 39:1546–1553. Preferably, GLP-1 is administered to the subject in the range of 1 to 5 pM/kg body weight/minute intravenously, or 0.1 to 5 nM/kg body weight subcutaneously. Depending upon the specific activity of the GLP-1 agonist (or antagonist) as compared to GLP-1(7–36) amide, the dosing regime may be adjusted up or down from that recommended for GLP-1(7–36) amide. For example, the results presented herein indicate that, on a per weight basis, exendin 4 is at least 20 times more potent than GLP-1(7–36) amide in the mammalian central nervous system. Therefore, exendin 4 is preferably administered to the subject in the range of 50 to 250 nM/kg body weight/minute intravenously, or to 200 $\mu$M/kg body weight subcutaneously.

Formulations and Use.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration. Additionally, as described below by way of example, compounds for use in the present invention may be delivered directly to the brain.

For delivery directly to the central nervous system, delivery techniques should be preferably designed to cross the blood-brain barrier. For example, agonists and antagonists may be appended to agents which facilitate crossing of the blood-brain barrier (see PCT W089/10134, which is incorporated by reference herein in its entirety). Alternatively, chemicals can be preadministered that make the blood brain barrier leaky to let peptides pass. Further, GLP-1 and exendin agonists and antagonists may be directly delivered to the brain, as shown below by way of a working in vivo example.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner. Examples of buccal formulations for GLP-1 are described in Gutniak et al., 1996, Diabetes Care 19:843. For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

EXAMPLES

EXAMPLE 1. Generation of GLP-1R$^{-/-}$ Mice

Mice mutant for the GLP-1R gene were generated as follows. A 16.2 kb GLP-1R gene fragment was cloned by plaque hybridization to the rat GLP-LR cDNA (Wheeler et al., 1993, Endocrinology 133:57–62, the disclosure of which is incorporated by reference) from a genomic mouse ES cell 129 I Dash library. pPNT (Tybulewicz et al., 1991, Cell 65:1153–1163) was used to construct a targeting vector by replacing two exons encoding the first and third transmembrane domains and intervening peptide sequence with a PGK-neo cassette in the same transcription orientation along with 4.8 and 3.5 kb of GLP-1R gene sequences 5' and 3' to the PGK-neo sequence, respectively.

The linearized construct was electroporated into ES cell line R1 according to the method of Nagy et al., 1993, in "Gene Targeting: A Practical Approach. (ed. Joyner, A.L.) pp. 147–178 (Oxford Univ. Press, Oxford). ES cell lines with one disrupted GLP-1R gene allele were aggregated with CD1 morulae to generate germline chimeras. GLP-1R$^{+/-}$ mice from separate litters were mated to obtain mice homozygous for the GLP-1R gene mutation.

Initially, the GLP-1R$^{-/-}$ mice appeared phenotypically normal. No significant difference in mean body weight was determined in GLP-1R$^{(-/-)}$ mice of different ages. No histological abnormality was observed following analysis of pancreas, lung, or brain obtained from GLP-1R$^{-/-}$ mice. However, closer inspection revealed the unexpected finding that the testes and ovaries in GLP-1R$^{-/-}$ mice are significantly and consistently smaller. This result implies that the GLP-1R$^{-/-}$ mice have a defective gonadal maturation. Further, the GLP-1R$^{-/-}$ mice exhibiting a significant (p<0.0001) delay of several days in reaching puberty, as assessed by age to vaginal opening. Involvement of the GLP-1/GLP-1R axis in mammalian sexual development was not known prior to analysis of the GLP-1R knockout mammals.

The GLP-1R$^{-/-}$ mice also showed an altered response to stress as compared to wild-type mice. For example, age matched wild-type and GLP-1R$^{-/-}$ mice were injected intraperitoneally with saline each day for two weeks. At the end of two weeks, the wild-type mice of this age had, as expected, consistently gained weight. However, the GLP-1R$^{-/-}$ mice actually lost weight. This result is contrary to what would be predicted if the GLP-1/GLP-1R axis was crucial to the control of satiety response in mammals.

EXAMPLE 2. Effects Of GLP-1 and Exendin Agonists And Antagonists On The Central Nervous System This experiment was designed to determine the effects of GLP-1 and exendin on central nervous system activity. In order to determine if these effects, if any, were transduced solely through the GLP-1R, both wild type mice, and GLP-1R$^{(-/-)}$ knockout mice were utilized.

Male CD1 mice were used for these experiments. Wild-type (+/+), male CD1 mice (approx. 11 weeks old) were obtained from Charles River Canada (Quebec). Mice were acclimatized to the animal facility for several days prior to use in the actual experiments.

GLP-1R$^{(-/-)}$ knockout age-matched male mice, produced as described above in example 1, were bred in the Toronto Hospital animal facility. All mice were fed a diet of ad libitum access to standard laboratory rat chow and tap water.

All mice were faster overnight 16 hours prior to the start of the experiment. Mice were lightly anesthetized by placing them in a covered beaker with 800 µl of Methoxyflurane (Metofane, Jannsen Pharmaceuticals) for approximately 3 minutes. Peptides were delivered into the ventricles by ICV injection using a 2.5 mm×30 gauge needle attached to a Hamilton syringe. All test peptides were dissolved in phosphate buffered saline. Mice were given 5 µl ICV injections of the test peptides or saline, following which they were observed closely for 3 hours.

Following ICV administration of GLP-1 [5 µg/5 µl; Glucagon-like Peptide 1 (7–36) amide, human, lot # AM680, Bachem California, Torrence, Calif.], Exendin (9–39) amide (10 µg/5 µl; lot # ZN136, Bachem California, Torrence, Calif.), Exendin-4 amide (15 µg/5 µl; kit # 506189, Bachem California, Torrence, Calif.), or PBS, mice were placed into individual cages for the period of observation.

To record food intake, mice were given a pre-weighed (approx. 3 g) amount of rodent chow when all members of a test group appeared fully alert, generally about 20–30 minutes after ICV injection.

Approximately 15–20 min. after the mice had begun to eat, or no longer than 30 min. following the addition of the pre-weighed rodent chow to the cages, the parameter of arousal/sedation was assessed, namely mice were assessed for locomotor activity by measuring the number of times each animal crossed over a line that was placed in the center of the cage (line test).

The Locomotor activity was assessed for 3×30 min consecutive periods. The data for the first 30 minutes observation period is shown in the accompanying FIG. 1.

All wildtype mice injected with exendin were visibly highly lethargic, and barely moved even with prodding. This is reflected by a clear and marked decreased number of line cross events, best seen at the 30 and 90 minutes time periods. GLP-1 injected mice also exhibited the same tendency, but exendin was far more potent. However, exendin(9–39) had the reverse effect; mice injected with exendin(9–39) exhibited greatly increased locomotor activity.

Remarkably, exendin 4 also induced lethargy and reduced movement in the GLP-1R knockout mice, whereas GLP-1 did not. Thus, there must exist a separate action and receptor for exendin. Exendin(9–39) also induced lethargy in the GLP-1R knockout mice. Although the effects of exendin (9–39) on the putative exendin receptor are unknown, these results suggest that while exendin(9–39) may act as an antagonist of the GLP-1R, it is an agonist of the exendin receptor.

In summary, ICV injection of either exendin 4 or GLP-1 produced a calming effect in mice, associated with visibly decreased activity and movement. Conversely, mice injected with an exendin/GLP-1 antagonist, or mice with a mutation in the GLP-1R exhibited increased arousal and hence increased movement.

EXAMPLE 3. Comparison of Glucose Tolerance and Feeding Behavior In Wild Type and GLP-1R Knockout Mice This experiment was designed to assess the physiological importance of GLP-1 as a regulator of feeding behavior and insulin secretion in both wild-type and GLP-1.

For glucose tolerance and insulin determinations, age and sex-matched mice were housed under a light/dark cycle of 12 hours. Mice were fasted a minimum of 18 hours prior to glucose challenge with 1.5 mg glucose per gram body weight orally or intraperitoneally. Blood was withdrawn and both glucose and insulin were determined as described in Schrocchi et al., 1996, Nature Med. 2:1254–1258, the disclosure of which is incorporated by reference herein in its entirety.

Compared to wild-type mice, the GLP-1R$^{(-/-)}$ knockout mice exhibited increased levels of blood glucose following oral glucose challenge in association with diminished levels of circulating insulin. It was surprising that they also exhibit abnormal levels of blood glucose following intraperitoneal glucose challenge.

The eating behavior of fasted (20 hour) wild-type and GLP-1R$^{-/-}$ was also examined. In four separate experiments, the mean 2 hour food intake after fasting was 1.48±0.78 and 1.16±0.11 grams in wild-type vs. null mice, respectively. Therefore, disruption of the GLP-1/GLP-1R signalling pathway is not associated with disturbances in body weight or appetite.

EXAMPLE 4. Exendin Is A More Potent Mammalian CNS Effector Than GLP-1.

A dose response experiment was performed to compare the specific activities of exendin and GLP-1 peptides. Additionally, this experiment was designed to eliminate the possibility that the sedative response was connected to any feeding behavior. Therefore, mice were not fasted prior to the experiment, and were instead allowed food and water ad libitum throughout their dark cycle. At the beginning of the light cycle, food was removed and peptides administered. Exendin or GLP-1 peptide, obtained as described above, were each injected ICV into normal wildtype mice at a concentration of 0.5, 1.0, 5.0 or 10.0 µg per 5 µl, and locomotor activity assessed as above.

Results showed that exendin is more potent than GLP-1. For example, after the control saline injection, the mean number line crossings is 66.8 (n=5 mice). For mice injected with the highest dose of GLP-1, 10 µg, the mean number of line crossings is 24 (n=4 mice). However, mice injected with the lowest dose of exendin, 0.5 µg, crossed the line a mean number of 11.5 times. Hence the lowest dose of exendin used here is more potent than the highest dose of GLP-1. Therefore, on a weight (µg) basis, exendin was at least 20-fold more potent than GLP-1.

The results of this dose response experiment, taken together with the previous data showing loss of the GLP-1 effect, but not exendin effect, in the GLP-1R$^{-/-}$ mice, again differentiates between the effects of exendin and GLP-1 and also implies separate actions/receptors for these peptides in the mammalian brain.

Furthermore, the sedative effects of GLP-1 and exendin 4 on mice were seen independent of fasting or the presence of food. Along with the results presented above, showing that disruption of the GLP-1/GLP-1R pathway does not cause obesity, this indicates that these agonists do not exert their effects through a satiety response.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method of sedating a mammalian subject in need thereof, comprising administering exendin-3, exendin-4, GLP-1, or an agonist of the GLP-1 receptor to the subject in an amount sufficient to produce a sedative or anti-anxiolytic effect on the subject.

2. The method of claim 1, wherein exendin-4 is administered to the subject.

3. The method of claim 1 or 2, wherein the exendin-3, exendin-4, GLP-1, or agonist of the GLP-1 receptor is administered intracerebroventricularly.

4. The method claim 3, wherein the mammalian subject is a human.

5. The method of claim 1 or 2, wherein the exendin-3, exendin-4, GLP-1, or agonist of the GLP-1 receptor is administered orally, subcutaneously, intramuscularly, or intravenously.

6. The method of claim 5, wherein the mammalian subject is a human.

7. The method of claim 2, wherein exendin-4 is administered to the subject in the range of 50 to 250 nanoMoles/kg body weight/minute intravenously, or 5 to 200 $\mu$M/kg body weight subcutaneously.

8. The method of claim 1, wherein the mammalian subject is suffering from an abnormality resulting in anxiety, aggression, psychosis, seizures, panic attacks, hysteria, or sleep disorders.

9. The method of claim 1, wherein GLP-1 is administered to the subject in the range of 1 to 5 pM/kg body weight/minute intravenously, or 0.1 to 5 nanoMoles/kg body weight subcutaneously.

10. The method of claim 1, 2, 8, 7 or 9, wherein the mammalian subject is a human.

\* \* \* \* \*